United States Patent
Kiemeneij et al.

(12) 
(10) Patent No.: US 11,284,905 B2
(45) Date of Patent: Mar. 29, 2022

(54) HEMOSTASIS DEVICES AND METHODS OF USE

(71) Applicants: Merit Medical Systems, Inc., South Jordan, UT (US); Ferdinand Kiemeneij, South Jordan, UT (US)

(72) Inventors: Ferdinand Kiemeneij, GB Bussum (NL); Tyler Rees, Draper, UT (US); Aaron Hopkinson, Herriman, UT (US)

(73) Assignees: Merit Medical Systems, Inc., South Jordan, UT (US); Ferdinand Kiemeneij, South Jordan, UT (US)

( * ) Notice: Subject to any disclaimer, the term of this patent is extended or adjusted under 35 U.S.C. 154(b) by 26 days.

(21) Appl. No.: 16/179,257

(22) Filed: Nov. 2, 2018

(65) Prior Publication Data
US 2019/0133602 A1 May 9, 2019

Related U.S. Application Data (60) Provisional application No. 62/625,626, filed on Feb. 2, 2018, provisional application No. 62/581,446, filed on Nov. 3, 2017.

(51) Int. Cl.
*A61B 17/135* (2006.01)
*A61B 17/132* (2006.01)
*A61M 39/06* (2006.01)

(52) U.S. Cl.
CPC ........ *A61B 17/135* (2013.01); *A61B 17/1325* (2013.01); *A61M 39/06* (2013.01)

(58) Field of Classification Search
CPC .......... A61F 5/05866; A61H 2205/065; A61H 39/04; A61B 2017/12004; A61B 17/135; A61B 17/1325; A61M 39/06
See application file for complete search history.

(56) References Cited

U.S. PATENT DOCUMENTS

| | | | |
|---|---|---|---|
| 1,281,653 A | 10/1918 | Plummer | |
| 2,332,107 A | 10/1943 | Nieburgs | |
| 3,050,064 A | 8/1962 | Moore et al. | |
| 4,390,519 A | 6/1983 | Sawyer | |
| 4,479,495 A | 10/1984 | Isaacson | |
| 4,557,262 A | 12/1985 | Snow | |
| 4,834,802 A | 5/1989 | Prier | |
| 5,139,512 A | 8/1992 | Dreiling et al. | |
| 5,269,803 A | 12/1993 | Geary et al. | |
| 5,304,186 A | 4/1994 | Semler et al. | |

(Continued)

FOREIGN PATENT DOCUMENTS

| | | |
|---|---|---|
| CN | 201205292 | 3/2009 |
| CN | 201861701 | 6/2011 |

(Continued)

OTHER PUBLICATIONS

Office Action dated Jan. 8, 2020 for U.S. Appl. No. 15/648,110.

(Continued)

*Primary Examiner* — George J Ulsh
(74) *Attorney, Agent, or Firm* — Stoel Rives LLP (57) ABSTRACT

A hemostasis device configured to apply a compressive force to a puncture site of a patient's vessel, such as an artery of the hand, wrist, or foot, is disclosed. The hemostasis device may comprise a plurality of bands used to position and maintain a compression member over the puncture site. The hemostasis device may also comprise an inflation port in fluid communication with an inflatable bladder.

15 Claims, 10 Drawing Sheets

(56) References Cited

U.S. PATENT DOCUMENTS

| | | |
|---|---|---|
| 5,304,201 A | 4/1994 | Rice |
| 5,613,491 A | 3/1997 | Kanner et al. |
| 5,695,520 A | 12/1997 | Bruckner et al. |
| 5,728,120 A | 3/1998 | Shani et al. |
| 5,779,657 A | 7/1998 | Daneshvar |
| 5,997,564 A | 12/1999 | Shehata et al. |
| 6,068,646 A | 5/2000 | Lam |
| 6,231,507 B1 | 5/2001 | Zikorus et al. |
| 6,647,986 B1 | 11/2003 | Korotko et al. |
| 6,833,001 B1 | 12/2004 | Chao |
| 7,758,574 B2 | 7/2010 | Hijii et al. |
| 7,780,612 B2 | 8/2010 | Ross |
| 8,147,417 B2 | 4/2012 | Gavriely |
| 8,632,840 B2 | 1/2014 | Avitable |
| 8,845,680 B2 | 9/2014 | Lampropoulos et al. |
| 9,332,994 B2 | 5/2016 | Pancholy et al. |
| D804,663 S | 12/2017 | Jenkins |
| 10,172,625 B2 | 1/2019 | Wada et al. |
| 10,463,833 B2 | 11/2019 | Clarke et al. |
| 10,492,797 B2 | 12/2019 | Okamura |
| D893,034 S | 8/2020 | Kase et al. |
| 2002/0188315 A1 | 12/2002 | Guzman et al. |
| 2003/0055453 A1 | 3/2003 | Akerfeldt |
| 2003/0139766 A1 | 7/2003 | McEwen et al. |
| 2003/0149359 A1 | 8/2003 | Smith |
| 2005/0113866 A1 | 5/2005 | Heinz et al. |
| 2005/0125025 A1 | 6/2005 | Rioux |
| 2006/0058841 A1 | 3/2006 | Mills et al. |
| 2006/0190026 A1 | 8/2006 | Sanders |
| 2007/0239092 A1 | 10/2007 | Ross |
| 2007/0248810 A1 | 10/2007 | McGee et al. |
| 2007/0270720 A1 | 11/2007 | Fry |
| 2009/0209896 A1 | 8/2009 | Selevan |
| 2009/0240182 A1 | 9/2009 | Weber et al. |
| 2009/0281565 A1 | 11/2009 | Mcneese |
| 2010/0211000 A1 | 8/2010 | Killion et al. |
| 2010/0217202 A1 | 8/2010 | Clark |
| 2010/0280541 A1 | 11/2010 | Lampropoulos |
| 2012/0221041 A1 | 8/2012 | Hansson et al. |
| 2012/0238934 A1 | 9/2012 | During |
| 2012/0296369 A1 | 11/2012 | Atthoff et al. |
| 2013/0023734 A1 | 1/2013 | Okamura |
| 2013/0079723 A1 | 3/2013 | Andino et al. |
| 2013/0165787 A1 | 6/2013 | Ukawa et al. |
| 2013/0237866 A1 | 9/2013 | Cohen |
| 2013/0245675 A1 | 9/2013 | Kaisha |
| 2013/0289613 A1 | 10/2013 | Kaisha |
| 2014/0012120 A1 | 1/2014 | Cohen et al. |
| 2014/0012313 A1 | 1/2014 | Finkielsztien et al. |
| 2014/0125718 A1 | 5/2014 | Morrison et al. |
| 2014/0142615 A1 | 5/2014 | Corrigan, Jr. |
| 2014/0236221 A1 | 8/2014 | Zhadkevich |
| 2014/0288408 A1 | 9/2014 | Deutsch |
| 2015/0018868 A1 | 1/2015 | Pancholy |
| 2015/0018869 A1 | 1/2015 | Benz et al. |
| 2015/0032149 A1 | 1/2015 | Croushorn et al. |
| 2015/0164436 A1 | 6/2015 | Maron et al. |
| 2015/0201948 A1 | 7/2015 | Kornowski et al. |
| 2015/0314074 A1 | 11/2015 | Howlett et al. |
| 2015/0327870 A1 | 11/2015 | Fortson et al. |
| 2015/0327871 A1 | 11/2015 | Fortson et al. |
| 2015/0342615 A1 | 12/2015 | Keinan et al. |
| 2016/0058988 A1 | 3/2016 | Kesten et al. |
| 2016/0183951 A1 | 6/2016 | Pancholy |
| 2017/0007807 A1 | 1/2017 | Weerakoon et al. |
| 2017/0273693 A1 | 9/2017 | Morrison et al. |
| 2018/0000494 A1 | 1/2018 | Wada et al. |
| 2018/0008281 A1 | 1/2018 | Hazama |
| 2018/0008282 A1 | 1/2018 | Hazama et al. |
| 2018/0008283 A1 | 1/2018 | Hazama |
| 2018/0014832 A1 | 1/2018 | Lampropoulos et al. |
| 2018/0028195 A1 | 2/2018 | Benz et al. |
| 2018/0042615 A1 | 2/2018 | Kimura et al. |
| 2018/0070956 A1 | 3/2018 | Lampropoulos et al. |
| 2018/0185032 A1 | 7/2018 | Matsushita et al. |
| 2018/0250017 A1 | 9/2018 | Matsushita et al. |
| 2018/0280008 A1 | 10/2018 | Okamura |
| 2019/0021742 A1 | 1/2019 | Hazama |
| 2019/0029693 A1 | 1/2019 | Okamura |
| 2019/0046214 A1 | 2/2019 | Hazama |
| 2019/0133604 A1 | 5/2019 | Maeda et al. |
| 2019/0133605 A1 | 5/2019 | Hazama et al. |
| 2019/0133606 A1 | 5/2019 | Hazama |
| 2019/0133607 A1 | 5/2019 | Hazama |
| 2019/0150938 A1 | 5/2019 | Hazama et al. |
| 2019/0274692 A1 | 9/2019 | Lampropoulos et al. |
| 2019/0314035 A1 | 10/2019 | Hopkinson et al. |
| 2020/0029946 A1 | 1/2020 | Green et al. |
| 2021/0052282 A1 | 2/2021 | Lampropoulos et al. |

FOREIGN PATENT DOCUMENTS

| | | |
|---|---|---|
| DE | 4006696 | 11/1990 |
| FR | 2828231 | 2/2003 |
| GB | 2109239 | 6/1983 |
| JP | 2012010823 | 1/2012 |
| JP | 2013111444 | 6/2013 |
| JP | 6211285 | 10/2014 |
| JP | 2014200308 | 10/2014 |
| JP | 6261368 | 8/2015 |
| JP | 2015150298 | 8/2015 |
| JP | 6389510 | 9/2015 |
| JP | 6261420 | 11/2015 |
| JP | 2015188608 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019058498 | 4/2019 |
| JP | 6544854 | 6/2019 |
| JP | 6559128 | 7/2019 |
| JP | 2019154915 | 9/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| JP | 6667234 | 2/2020 |
| JP | 202018686 | 2/2020 |
| JP | 202022679 | 2/2020 |
| JP | 202039815 | 3/2020 |
| JP | 202039816 | 3/2020 |
| WO | 199855072 | 12/1998 |
| WO | 2004041313 | 5/2004 |
| WO | 2017043536 | 3/2017 |
| WO | 2015141786 | 4/2017 |
| WO | 2018017365 | 1/2018 |

OTHER PUBLICATIONS

European Search Report dated Sep. 7, 2017 for EP 09763115.4.
International Search Report and Written Opinion dated Nov. 28, 2017 for PCT/US2017/041726.
International Search Report and Written Opinion dated Dec. 26, 2017 for PCT/US2017/051715.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.
Notice of Allowance dated Jun. 9, 2014 for U.S. Appl. No. 13/741,046.
Notice of Allowance dated Oct. 16, 2012 for U.S. Appl. No. 12/435,227.
Office Action dated Feb. 14, 2014 for U.S. Appl. No. 13/741,046.
Office Action dated Mar. 2, 2011 for U.S. Appl. No. 12/349,405.
Office Action dated Mar. 5, 2013 for U.S. Appl. No. 13/741,046.

(56) References Cited

OTHER PUBLICATIONS

Office Action dated Jun. 6, 2016 for U.S. Appl. No. 14/033,177.
Office Action dated Jun. 28, 2011 for U.S. Appl. No. 12/349,405.
Office Action dated Aug. 17, 2012 for U.S. Appl. No. 12/349,405.
Office Action dated Nov. 3, 2015 for U.S. Appl. No. 14/033,177.
Office Action dated Dec. 8, 2011 for U.S. Appl. No. 12/349,405.
Office Action dated Dec. 27, 2016 for U.S. Appl. No. 14/033,177.
Office Action dated Jan. 10, 2019 for U.S. Appl. No. 15/705,759.
International Search Report and Written Opinion dated Jul. 30, 2019 for PCT/US2019/026785.
International Search Report and Written Opinion dated May 14, 2019 for PCT/US2018/058992.
International Search Report and Written Opinion dated Jun. 12, 2019 for PCT/US2019/020980.
Office Action dated May 28, 2019 for U.S. Appl. No. 15/648,110.
Pua, et al.,"Snuffbox" Distal Radial Access, J Vasc Interv Radiol, No. 29:44 ,2018.
Zhou, et al., Transient Ulnar Artery Compression Facilitates Transradial Access, Medicine, No. 95:48 ,2016.
European Search Report dated Feb. 27, 2020 for EP17851579.7.
Merit Medical Adds 2 New Products for Assisting Hemostasis, Posted at Merit.com, no posting date, retrieved Aug. 26, 2020 online https://www.merit.com/articles/merit-medical-adds-2-new-products-assisting-hemostasis (2020).
Office Action dated Sep. 16, 2020 for U.S. Appl. No. 16/380,505.
Office Action dated Sep. 6, 2019 for U.S. Appl. No. 15/705,759.
Office Action dated Feb. 16, 2021 for U.S. Appl. No. 16/380,505.
Notice of Allowance dated Nov. 25, 2020 for U.S. Appl. No. 29/653,828.
European Search Report dated Apr. 23, 2021 for EP18872642.6.
Office Action dated May 10, 2021 for U.S. Appl. No. 16/294,020.
Office Action dated May 25, 2021 for U.S. Appl. No. 16/380,505.
International Search Report and Written Opinion dated Apr. 2, 2019 for PCT/US2018/060089.
Extended European Search Report dated Oct. 28, 2021 for EP19763606.1.
Notice of Allowance dated Sep. 9, 2021 for U.S. Appl. No. 16/294,020.
Office Action dated Sep. 14, 2021 for U.S. Appl. No. 16/921,343.

HEMOSTASIS DEVICES AND METHODS OF USE

RELATED APPLICATIONS

This application claims priority to U.S. Provisional Application No. 62/581,446, filed on Nov. 3, 2017 and titled "Hemostasis Devices and Methods of Use," and U.S. Provisional Application No. 62/625,626, filed on Feb. 2, 2018 and titled "Hemostasis Devices and Methods of Use," both of which are hereby incorporated by reference in their entireties.

TECHNICAL FIELD

The present disclosure relates generally to the field of medical devices used to provide hemostasis at a vascular access puncture site. More particularly, some embodiments of the present disclosure relate to a hemostasis device used to provide hemostasis of the arteries of the wrist and foot, including the distal radial artery, following vascular access.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Interventional vascular procedures may be performed for both diagnostic and therapeutic reasons. Some vascular interventional procedures require percutaneous access of a vessel, such as an artery, with a needle followed by insertion of guidewires, dilators, sheaths, catheters, etc. The vessel to be accessed may be a peripheral artery of the arm, hand, or foot. For example, the peripheral artery may be the distal radial artery located within the anatomical snuffbox of the hand. The vessel access creates a puncture site or hole in the vessel wall through which medical devices may be passed during a procedure. At the conclusion of the procedure, the procedural devices may be removed and pressure or compression may then be applied to the puncture site until hemostasis is achieved. The compression may be applied by a healthcare worker or by a hemostasis device, such as the hemostasis devices described herein. Such hemostasis devices may comprise bands for securement of the device to a patient and a compression member to apply a pressure or compressive force to the puncture site.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic. Thus, two components may be coupled to each other even though they are not in direct contact with each other. The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

The anatomical snuffbox is defined as a hollow located on a thumbside of a back of a hand when a thumb is extended fully. As used herein, the back of the hand refers to the dorsal side of the hand, or the side opposite the palm. The palmside is the ventral side, opposite the dorsal side. "Thumbside" refers to the lateral side of the hand adjacent to the thumb.

"Fluid" is used in its broadest sense, to refer to any fluid, including both liquids and gases as well as solutions, compounds, suspensions, etc., which generally behave as fluids.

Figure 1:
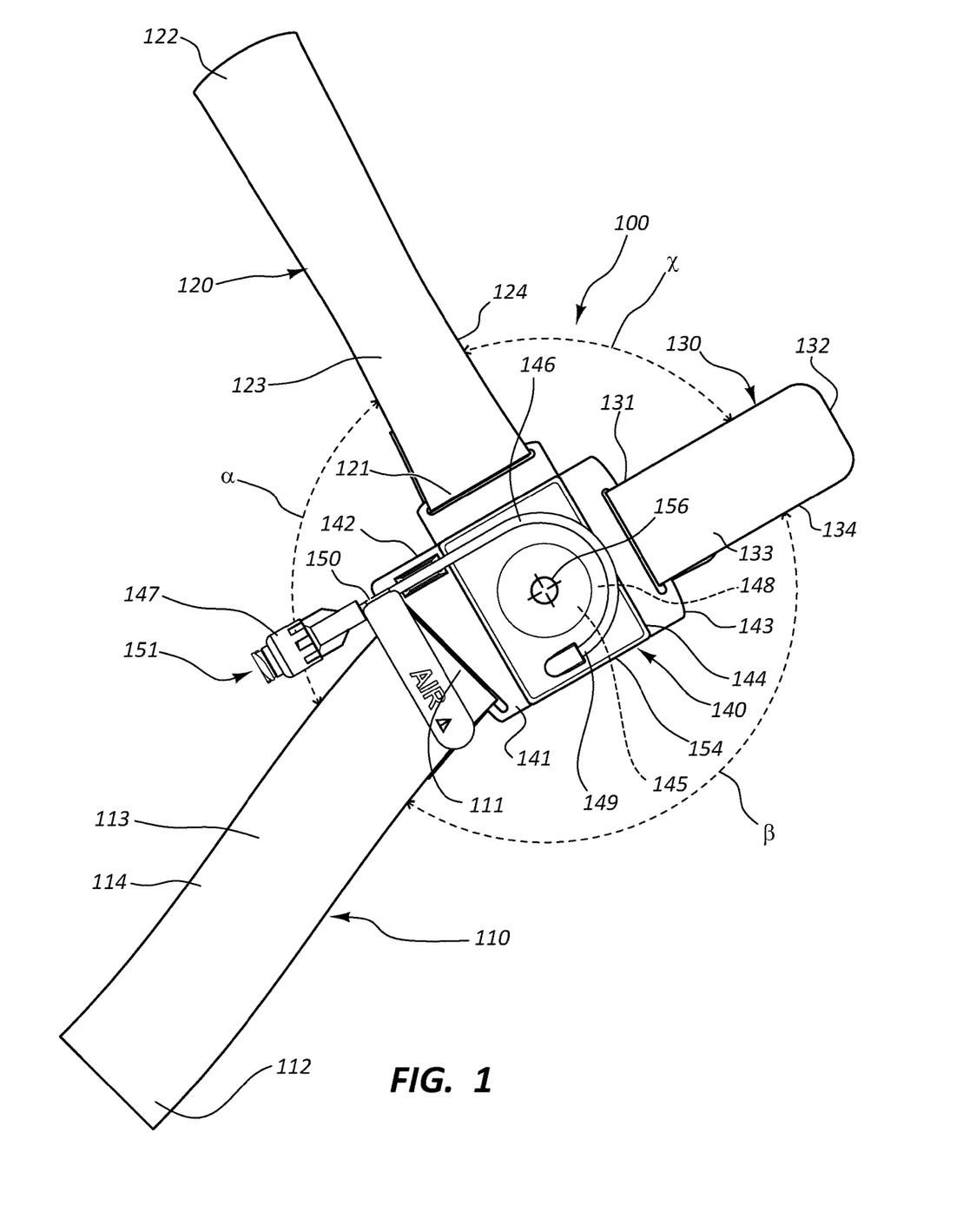
FIG. 1 is a top view of a hemostasis device.

FIG. 1 provides a view of a vascular access hemostasis device, system, or assembly 100. The hemostasis device 100 may comprise a hand band or strap 110, a thumb band or strap 120, a securement band or strap 130, and a compression member 140. The hemostasis device 100 may be configured to fit around a proximal portion of a hand and around a thumb to provide compression to a vascular access puncture site of a distal portion of a radial artery in the anatomical snuffbox area of a patient's hand. The hemostasis device 100 may be configured to be a left hand device or a right hand device such that the hemostasis device 100 may provide hemostasis at a distal radial artery puncture site in the left or right hand. FIG. 1 illustrates a hemostasis device configured for use on the left hand of the patient. In some embodiments, the hemostasis device 100 may comprise additional bands to facilitate coupling of the hemostasis device 100 to the hand.

With continued reference to FIG. 1, the bands 110, 120, 130 may be formed from a flexible material, such as a plastic film, cloth, etc. The bands 110, 120, 130 may comprise a releasable securement mechanism, such as a hook-and-loop material comprising a loop material configured to attach to a hook material. In some embodiments, the hook material and/or the loop material may be integral to the material of the bands 110, 120, 130. In other embodiments, the hook material and/or the loop material may be coupled to a surface of the band 110, 120, 130. The hook material and/or the loop material may cover a top surface and/or a bottom surface of the bands 110, 120, 130. In other embodiments, the hook material and/or the loop material may cover a portion of the top surface and/or the bottom surface of the bands 110, 120, 130. Other types of releasable securement mechanisms, such as pressure sensitive adhesives, buckles, magnets, snaps, clasps, etc. are contemplated to be within the scope of this disclosure.

In the illustrated embodiment, the hand band 110 comprises a first end 111, a second end 112, and a body portion 113. In some embodiments, the first end 111 of the hand band 110 may be coupled to the compression member 140. The hand band 110 may be coupled to a first side 141 of the compression member 140 by wrapping a portion of the first end 111 around a portion of the first side 141. In other embodiments, the hand band 110 may be coupled to the compression member 140 using any suitable technique, such as heat welding, sonic welding, gluing, mechanical compression, etc.

The hand band 110 may be fixedly coupled to the compression member 140 such that the hand band 110 extends outwardly from the compression member 140 at an angle α relative to the thumb band 120 and angle β relative to the securement band 130. Angle α may range from 15 degrees to 120 degrees, including 30 degrees to 110 degrees, 70 degrees to 120 degrees, 90 degrees to 120 degrees, or ranges including angles of greater than 90 degrees, greater than 100 degrees, and greater than 110 degrees. Angle β may range from 120 degrees to 180 degrees including 140 degrees to 170 degrees, 150 degrees to 160 degrees, or ranges of 180 degrees or less, 170 degrees or less, and 160 degrees or less. In some embodiments, the hand band 110 may be pivotably coupled to the compression member 140, such that the hand band 110 angles α, β are adjustable. In some such embodiments, the hand band 110 may be configured to rotate freely. In other words, the hand band 110 may be configured to rotate a full 360 degrees with respect to the compression member 140. In other embodiments, the hand band 110 may be configured to rotate from one degree to 180 degrees, including 30 degrees to 150 degrees. In use, a practitioner may rotate the hand band 110 with respect to the compression member 140 in order to match or conform to the anatomy or characteristics of a particular patient.

The body 113 of the hand band 110 may form a rectangular shape with a long edge 114 extending away from the compression member 140. The long edge 114 may comprise a concave portion such that the hand band 110 forms an "hour glass" shape. The second end 112 may comprise rounded corners such that the second end 112 is atraumatic to the skin of the patient.

In some embodiments, the thumb band 120 comprises a first end 121, a second end 122, and a body portion 123. The thumb band 120 may be configured to prevent proximal displacement of the hemostasis device 100 from the patient's hand. The thumb band 120 may be formed from a flexible material, such as a plastic film, cloth, etc. In some embodiments, the first end 121 of the thumb band 120 may be fixedly coupled to a second side 142 of the compression member 140. The thumb band 120 may be coupled to the second side 142 of the compression member 140 by wrapping a portion of the first end 121 around a portion of the second side 142. In other embodiments, the thumb band 120 may be coupled to the compression member 140 using any suitable technique, such as heat welding, sonic welding, gluing, mechanical compression, etc.

The thumb band 120 may be fixedly coupled to the compression member 140 such that the thumb band 120 extends outwardly from the second side 142 of the compression member 140 between the hand band 110 and the securement band 130 at an angle α relative to the hand band 110 and angle χ relative to the securement band 130. Angle χ may range from 15 degrees to 120 degrees, including 30 degrees to 110 degrees, 70 degrees to 100 degrees or ranges of 90 degrees plus or minus 10 degrees. In some embodiments, the thumb band 120 may be pivotably coupled to the compression member 140, such that angles α,χ are adjustable. In some such embodiments, the thumb band 120 may be configured to rotate freely. In other words, the thumb band 120 may be configured to rotate a full 360 degrees with respect to the compression member 140. In other embodiments, the thumb band 120 may be configured to rotate from one degree to 180 degrees, including 30 degrees to 150 degrees. In use, a practitioner may rotate the thumb band 120 with respect to the compression member 140 in order to match or conform to the anatomy or characteristics of a particular patient.

The body 123 of the thumb band 120 may form a rectangular shape with a long edge 124 extending away from the compression member 140. The long edge 124 may comprise a concave portion such that the thumb band 120 forms an "hour glass" shape. The second end 122 may comprise rounded corners such that the second end 122 is atraumatic to the skin of the patient.

In some embodiments, the securement band 130 comprises a first end 131, a second end 132, and a body portion 133. The securement band 130 may be formed from a flexible material, such as a plastic film, cloth, etc. In some embodiments, the first end 131 of the securement band 130 may be fixedly coupled to the compression member 140. The securement band 130 may be coupled to a third side 143 of the compression member 140 by wrapping a portion of the first end 131 around a portion of the third side 143. In other embodiments, the securement band 130 may be coupled to the compression member 140 using any suitable technique, such as heat welding, sonic welding, gluing, mechanical compression, etc.

The securement band 130 may be fixedly coupled to the compression member 140 such that the securement band 130 extends outwardly from the compression member 140 between the hand band 110 and the thumb band 120. In some embodiments, the securement band 130 may extend outwardly from the third side 143 of the compression member 140 at angle β relative to the hand band 110 and angle χ relative to the thumb band 120. In some embodiments, securement band 130 may be pivotably coupled to the compression member 140, such that the securement band 130 angle is adjustable over a continuous range. In some such embodiments, the securement band 130 may be configured to rotate freely. In other words, the securement band 130 may be configured to rotate a full 360 degrees with respect to the compression member 140. In other embodiments, the securement band 130 may be configured to rotate from one degree to 180 degrees, including 30 degrees to 150 degrees. In use, a practitioner may rotate the securement band 130 with respect to the compression member 140 in order to match or conform to the anatomy or characteristics of a particular patient.

In certain embodiments, the hemostasis device 100 may not include a securement band 130. In such embodiments, the hand band 110 may extend from the first side 141 of the compression member 140 to the third side 143 of the compression member 140 such that the second end 112 of the hand band may be configured to be coupled to the third side 143 of the compression member 140 by a healthcare worker. In such embodiments, the second end 122 of the thumb band 120 may be coupled to the hand band 110. In other embodiments, the hand band 110 and/or the thumb band 120 may comprise an elastomeric material wherein the first end 111 is coupled to the first side 141 and the second end 112 is coupled to the third side 143 and the first end 121 is coupled to the second side 142 and the second end 122 is coupled to a fourth side 154 prior to use, such that the hand band 110 forms a first loop and the thumb band forms a second loop. In use, the four fingers of the patient's hand may be slid through the first loop and the patient's thumb may be slid through the second loop, such that the hemostasis device 100 is secured to the patient's hand.

The body 133 of the securement band 130 may form a rectangular shape with a long edge 134 extending away from the compression member 140. The second end 132 may comprise rounded corners such that the second end 132 is atraumatic to the skin of the patient.

With continued reference to FIG. 1, the compression member 140 may be configured to be positioned over the vascular access puncture site on the hand of a patient. The compression member 140 may be configured to be inflatable as illustrated in the embodiment of FIG. 1. In some embodiments, the compression member 140 may be configured to provide compression using a mechanical system including rigid compression pads, resilient or elastomeric compression pads, and/or mechanisms configured to displace the pads such as a threaded post. In other embodiments, the compression member 140 may comprise at least one gauze pad. In still other embodiments, the compression member 140 may be configured to compress the vascular access puncture site using any suitable mechanism.

As illustrated in FIG. 1, the compression member 140 may comprise a housing 144, an inflatable bladder 145, an inflation tube 146, and an inflatable port 147. The housing 144 may comprise the first side 141, the second side 142, and the third side 143, wherein the sides 141, 142, 143 are configured to be coupled to the hand band 110, the thumb band 120, and the securement band 130, respectively, as described previously. The housing 144 may be formed in a concave shape relative to a top surface such that the housing 144 conforms to an anatomical shape of the snuffbox area of the hand. The housing 144 may be transparent or translucent such that the puncture site can be seen through the housing 144. A target 156 image may be printed on either the top surface or a bottom surface of the housing or on a surface of the bladder (see, for example, discussion of element 256 of the embodiment of FIG. 5A. The target 156 may be configured to facilitate placement of the inflatable bladder 145 directly over the puncture site. The housing may be formed from any suitable transparent or translucent, rigid plastic material, such as polycarbonate, polystyrene, styrene copolymers, polyethylene teraphthalate, acrylic, polyethylene, polypropylene, etc.

The inflatable bladder 145 may comprise a flexible wall 148 configured to extend downward from the housing 144 when the bladder 145 is filled with air or fluid such that a compressive force may be applied to the vascular access puncture site. The bladder 145 may be sealed at its edges to the bottom surface of the housing 144. The bladder 145 may be transparent or translucent such that the puncture site can be seen through the flexible wall 148. The bladder 145 may be formed from any suitable, flexible, transparent or translucent material, such as polyethylene, polypropylene, etc. The fluid may comprise sterile water, normal saline solution, or any other suitable medical fluid.

In some embodiments, the inflation tube 146 may be fluidly coupled to the bladder 145 at a first end 149 and to the inflation port 147 at a second end 150 such that the inflation port 147 is in fluid communication with the bladder 145. The inflation port 147 may comprise a normally closed valve 151. The inflation port 147 may be configured to be releasably coupled to a medical device, such as a syringe (not shown). When coupled to the syringe, the valve 151 is opened and air or fluid may be injected into the bladder 145 to inflate the compression member 140. In certain embodiments air or fluid may be removed from the bladder 145 to deflate the compression member 140.

In some embodiments, a diagnostic or interventional procedure may be performed by the healthcare worker on the patient where access to the distal radial artery in the anatomical snuffbox area of the left hand is achieved utilizing a needle. The distal radial artery of the left hand may be chosen by the healthcare worker to avoid discomfort to the right hand of a right handed patient, to protect the radial artery near the wrist from trauma caused by the procedure, and to facilitate use of the right hand of a right handed healthcare worker while accessing the left distal radial artery. Additionally, the equipment in a surgical suite may be set up on the right side of the patient. Accessing the distal radial artery of the left hand allows the patient to comfortably lay his or her arm across the abdomen. In other embodiments, the healthcare worker may choose to access a patient's vascular system at any suitable site based on specific patient conditions.

Figure 2:
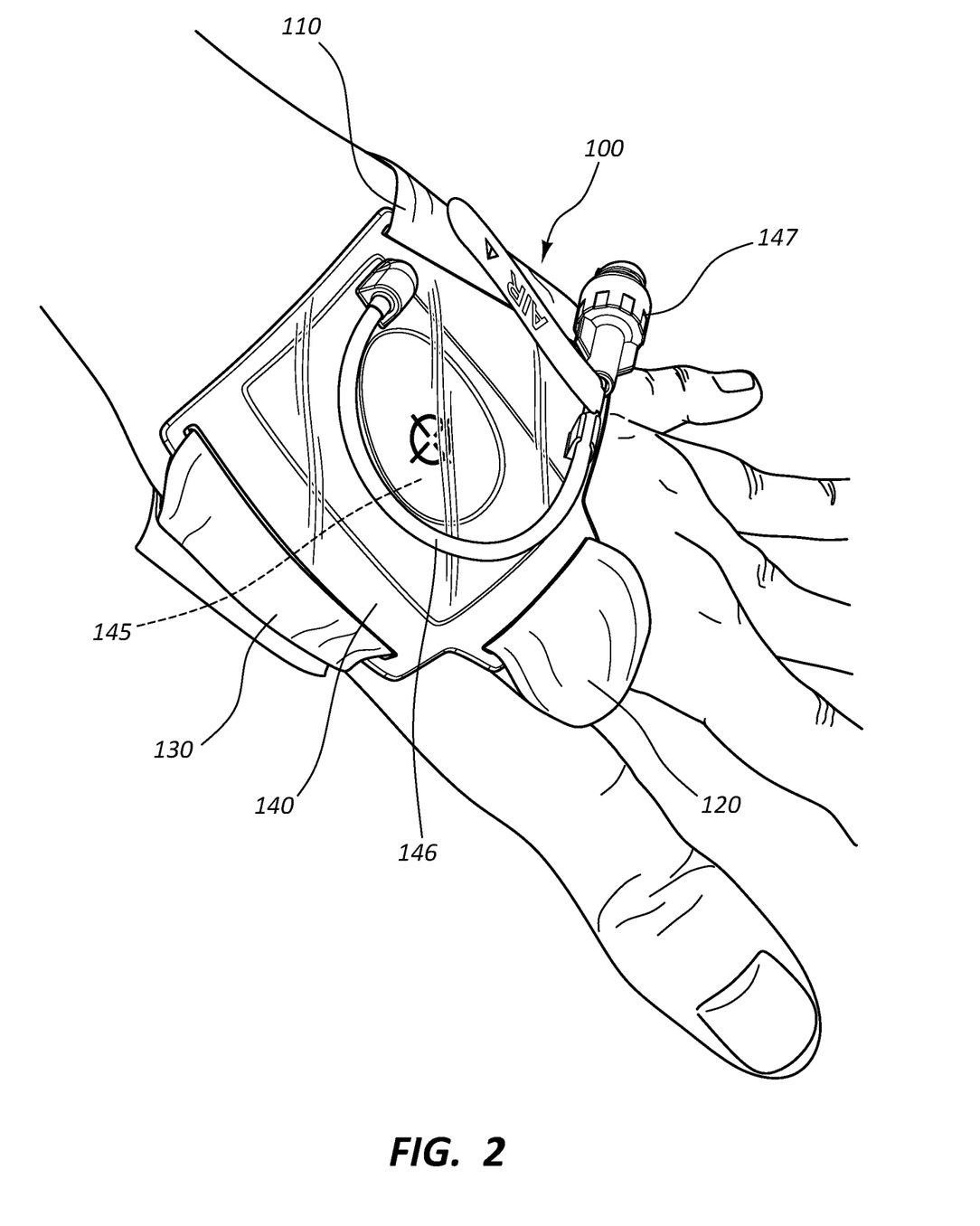
FIG. 2 is a view of a back of a hand with the hemostasis device positioned over a puncture site of a distal radial artery.
Figure 3:
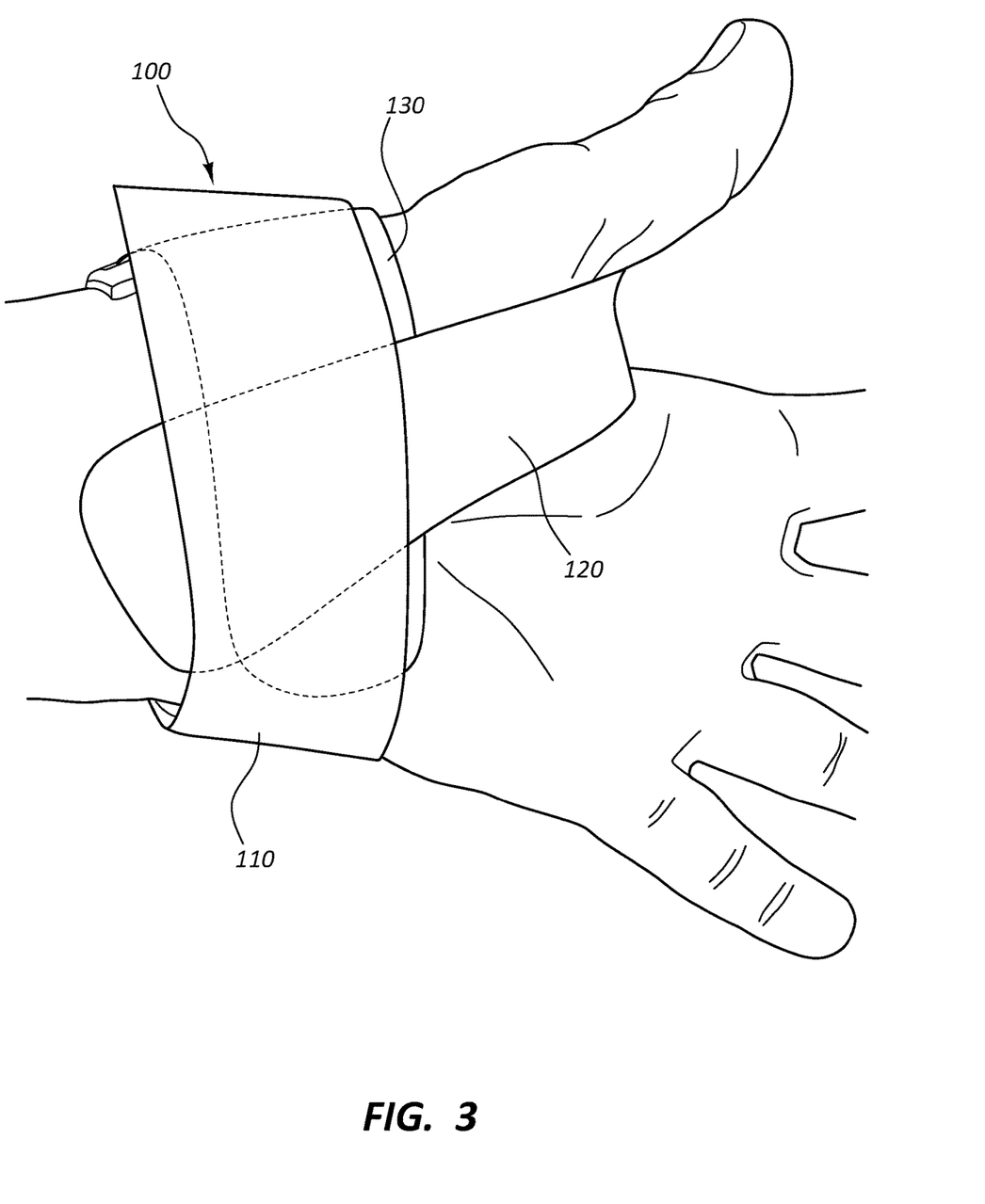
FIG. 3 is a view of a palm side of a hand with bands of the hemostasis device wrapped around the hand.

At the conclusion of the diagnostic or interventional procedure, compressive pressure or force may be applied to the puncture site of the distal radial artery to facilitate hemostasis of the puncture site as quickly as possible and without loss of a significant blood volume. Referring to FIGS. 2 and 3, the hemostasis device 100 may be utilized to apply the compressive pressure to the puncture site. In use, the compression member 140 may be positioned over the puncture site at the anatomical snuffbox of the hand. The hand band 110 may be extend toward a lateral side of the hand away from the thumb on the back or ventral side of the hand. The thumb band 120 may extend toward a space between the thumb and a first finger. The securement band 130 may extend to a lateral side of the hand adjacent to the thumb. The hand band 110 may be wrapped around the hand and the second end 112 coupled to the second end 132 of the securement band 130 on the dorsal side of the hand. The thumb band 120 may be wrapped around the base of the thumb and the second end 122 coupled to the securement band 130 on the dorsal side of the hand. Following placement of the hemostasis device 100, the syringe (not shown) may be coupled to the inflation port 147 and air or fluid is injected through the inflation tube 146 into the bladder 145 such that the bladder 145 is inflated and applies a compressive pressure or force to the puncture site. In some embodiments, the syringe may be coupled to the inflation port 147 to remove a portion of the air or fluid within the bladder 145 such that the bladder 145 is partially deflated. In other embodiments, the syringe may be coupled to the inflation port 147 to remove all of the air or fluid within the bladder 145 such that the bladder is fully deflated.

FIGS. 4A-10 depict an embodiment of a hemostasis device 200 that resembles the hemostasis device 100 described above in certain respects. Accordingly, like features are designated with like reference numerals, with the leading digits incremented to "2." For example, the embodiment depicted in FIGS. 4A-10 includes a hand band 210 that may, in some respects, resemble the hand band 110 of FIG. 1. Relevant disclosure set forth above regarding similarly identified features thus may not be repeated hereafter. Moreover, specific features of the hemostasis device 100 and related components shown in FIGS. 1-3 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the hemostasis device 200 and related components depicted in FIGS. 4A-11. Any suitable combination of the features, and variations of the same, described with respect to the hemostasis device 100 and related components illustrated in FIGS. 1-3 can be employed with the hemostasis device 200 and related components of FIGS. 4A-11, and vice versa. This pattern of disclosure applies equally to further embodiments depicted in subsequent figures and described hereafter, wherein the leading digits may be further incremented.

Figure 4A:
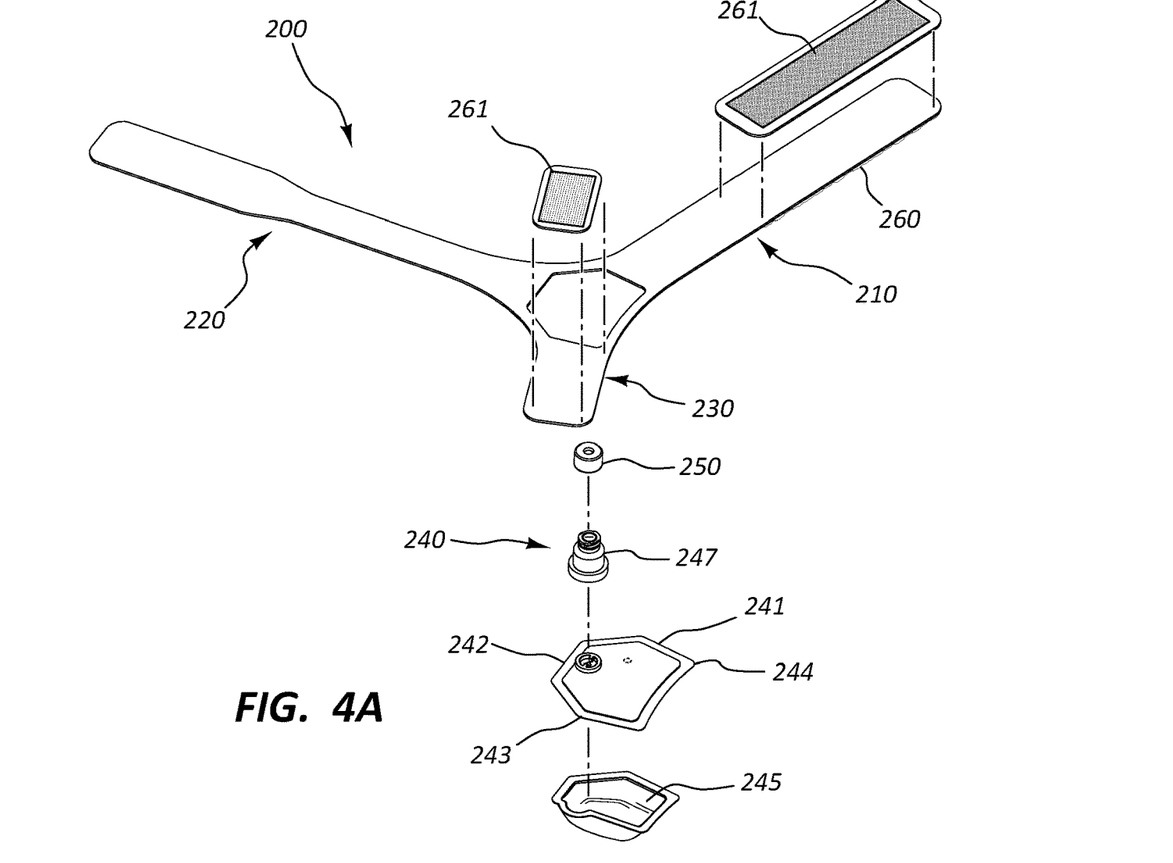
FIG. 4A is an exploded perspective view of a second hemostasis device.
Figure 4B:
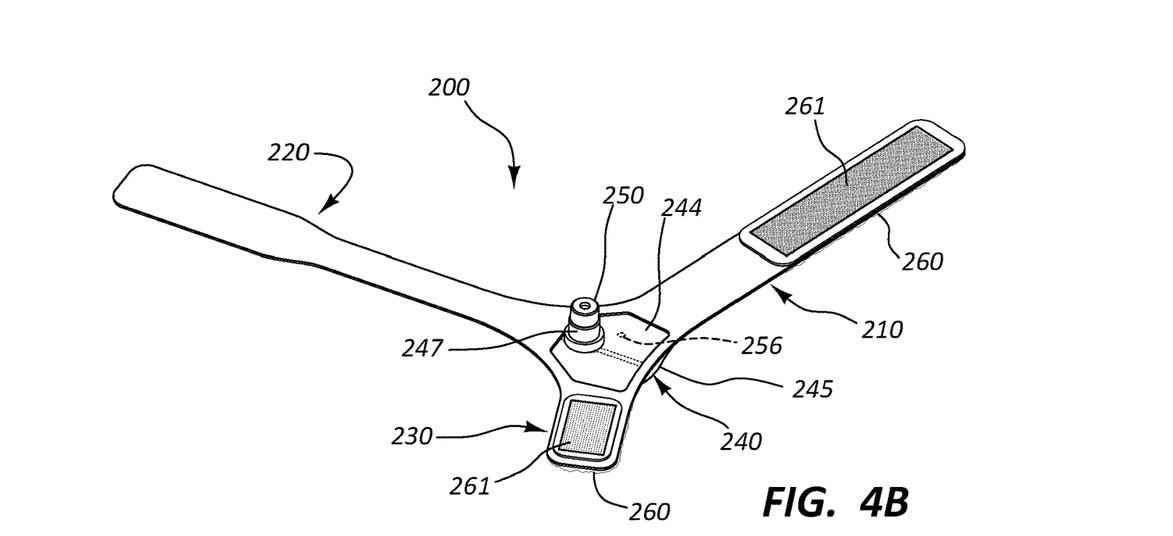
FIG. 4B is a perspective view of the hemostasis device of FIG. 4A.

FIG. 4A provides a perspective, exploded view of a vascular access hemostasis device, system, or assembly 200. FIG. 4B provides a perspective view of the hemostasis device 200. Referring to FIGS. 4A and 4B, the hemostasis device 200 may comprise a hand band or strap 210, a thumb band or strap 220, a securement band or strap 230, and a compression member 240. In some embodiments, the hand band 210, the thumb band 220, and the securement band 230 may be integrally formed, wherein the bands 210, 220, 230 may be cut, such as die cut, laser cut, hot wire cut, blade cut, etc. from a sheet of flexible material. In other embodiments, the bands 210, 220, 230 may be separately coupled to the compression member 240.

Figures 5A, 5B:
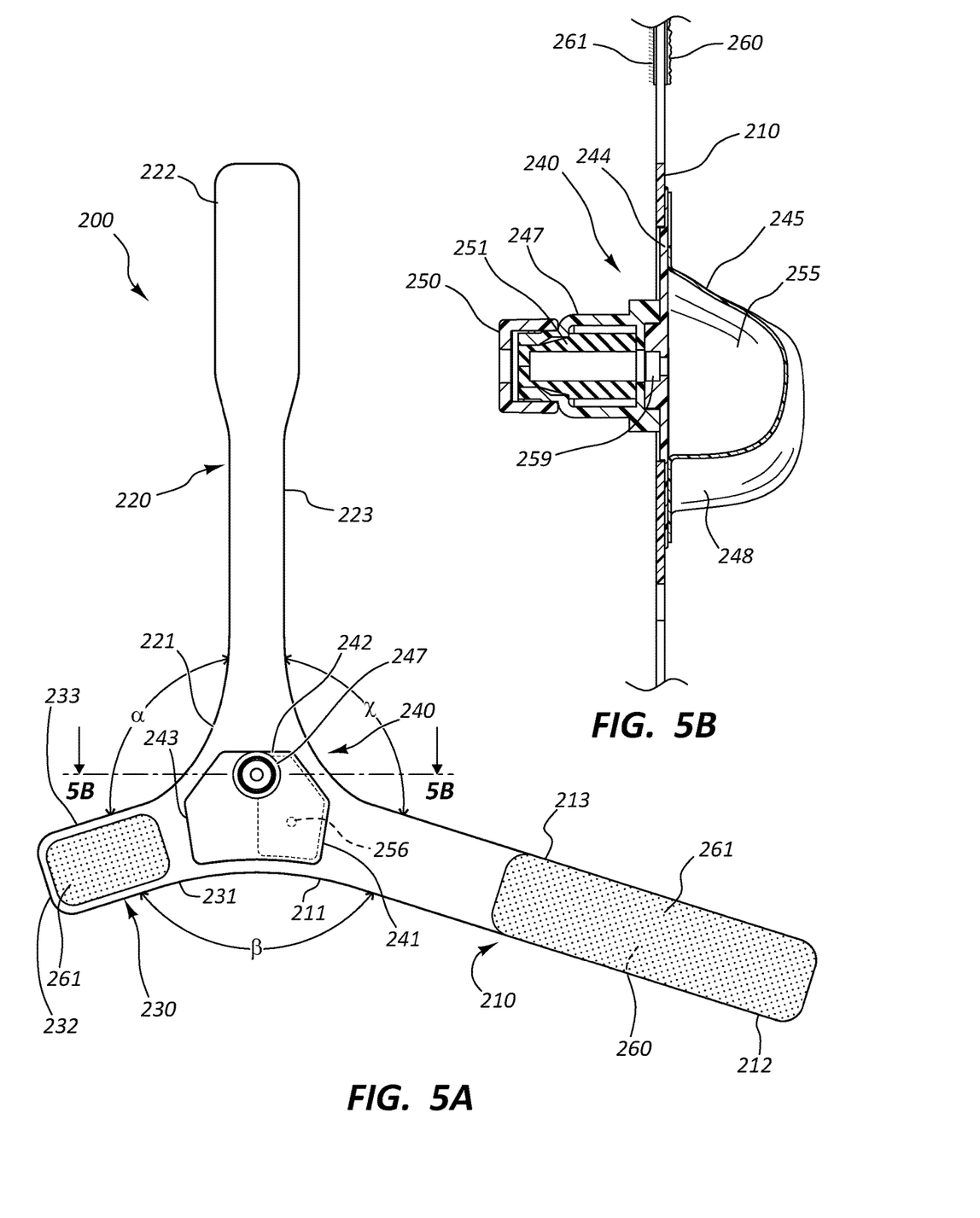
FIG. 5A is a top view of the hemostasis device of FIG. 4A.
FIG. 5B is a cross-sectional side view of the hemostasis device of FIG. 5A through section line 5B-5B.

FIG. 5A illustrates a top view of the hemostasis device 200. FIG. 5B is a cross-sectional view of the hemostasis device 200 through sectioning line 5B-5B. Referring to FIGS. 4A-5B, the compression member 240 may be configured to be positioned over the vascular access puncture site of a patient. The compression member 240 may be configured to be inflatable with air or fluid as shown in FIG. 5B. In some embodiments, the compression member 240 may be configured to provide compression using a mechanical system including rigid compression pads, resilient or elastomeric compression pads, and/or mechanisms configured to displace the pads such as a threaded post. In other embodiments, the compression member 240 may comprise at least one gauze pad. In still other embodiments, the compression member 240 may be configured to compress the vascular access puncture site using any suitable mechanism.

The compression member 240 may comprise a top plate 244, an inflatable bladder 245, and an inflation port 247. The top plate 244 may comprise a first side 241, a second side 242, and a third side 243, wherein the sides 241, 242, 243 are configured to be coupled to the hand band 210, the thumb band 220, and the securement band 230, respectively. The top plate 244 may be configured to be semi-flexible such that the top plate 244 may conform, at least partly, to an external anatomy of a patient where the hemostasis device 200 is placed, such as the hand, wrist, or foot. The top plate 244 may be transparent or translucent such that the puncture site can be seen through the top plate 244 to determine proper placement of the inflatable bladder 245 and hemostasis status during treatment. The top plate 244 may be formed of any suitable semi-flexible material such as polyethylene, polypropylene, polyvinyl chloride, etc.

The inflatable bladder 245 may be coupled to a bottom portion of the top plate 244 such that edges of the bladder 245 form an air or fluid tight seal. The inflatable bladder 245 may comprise a flexible wall 248 configured to extend downward from the top plate 244 to form an inflation chamber 255 when the bladder 245 is filled with air or fluid such that a compressive force may be applied to the vascular access puncture site. In some embodiments, the inflation chamber 255 may be configured to cover a portion of the bottom surface of the top plate 244. The inflation chamber 255 may be configured to cover either the left half or the right half of the top plate 244 such that the hemostasis device 200 may be configured as a left hand or right hand device. In other embodiments, the inflation chamber 255 may be configured to cover the full bottom surface of the top plate 244. The edges of the bladder 245 may be sealed to the bottom surface of the top plate using any suitable technique such as sonic welding, heat welding, adhesives, etc. The bladder 245 may be transparent or translucent such that the puncture site can be seen through the top plate 244 and the bladder 245 to determine proper placement of the inflatable bladder 245 over the puncture site and hemostasis status during treatment. The bladder 245 may comprise a target 256 printed on or adhered to a surface of the bladder 245, including a bottom surface of the bladder 245. The target 256 may be configured to facilitate placement of the bladder 245 over the puncture site. The bladder 245 may be formed from a flexible, translucent or transparent material such as polyethylene, polypropylene, polyvinyl chloride, etc.

The inflation port 247 may be configured to reduce a risk of inadvertent injection of air into an IV line by eliminating an extension tube between the compression member 240 and the inflation port 247. For example, if the inflation port 247 was coupled to an end of an extension tube, the inflation port 247 may be mistakenly used by a healthcare worker as an injection site for an IV line. If used mistakenly, excess fluid may be injected into the compression member resulting in a burst bladder 245 or excessive pressure at the puncture site causing tissue damage. Also, air intended to be injected to inflate the bladder may be inadvertently injected into an IV line resulting in potential morbidity or death of the patient. Additionally, the inflation port 247 may improve convenience of inflating the compression member 240 by providing the inflation port 247 directly coupled to the compression member 240 without an extension tube.

The inflation port 247 may be coupled to the top surface of the top plate 244 such that the inflation port 247 is in fluid communication with the inflation chamber 255 of the inflation bladder 245 through an orifice 259. The inflation port 247 may be positioned on the top plate 244 such that the inflation port 247 is in fluid communication with the inflation chamber 255 positioned on the left side, on the right side, or with full coverage of the top plate 244. The inflation port 247 may be positioned toward an outer perimeter of the inflation chamber 255 such that the inflation port 247 does not obstruct visualization of the target 256 and puncture site.

Figure 6:
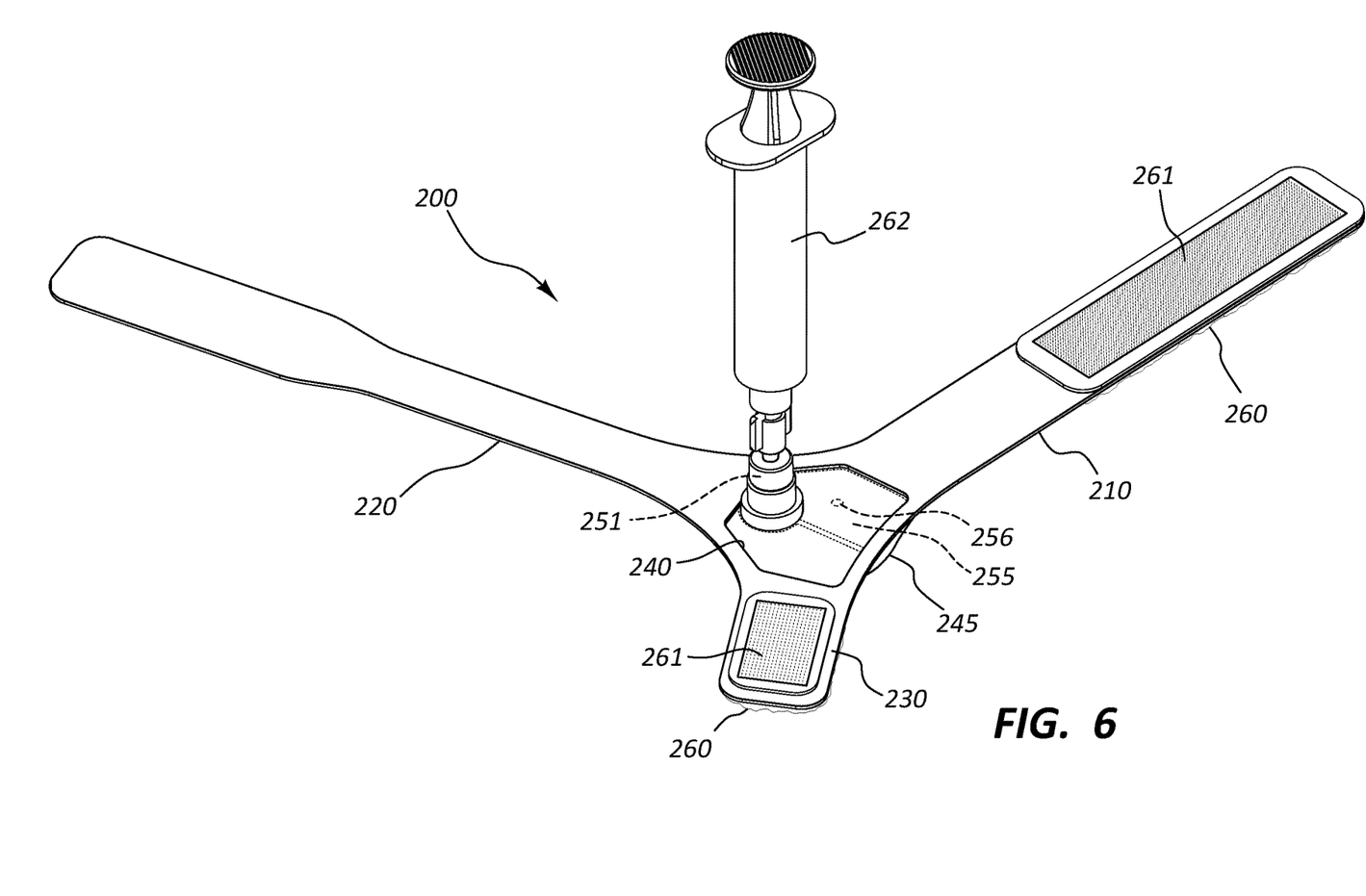
FIG. 6 is a perspective view of the hemostasis device of FIG. 4A with a syringe attached to an inflation port.
Figure 7:
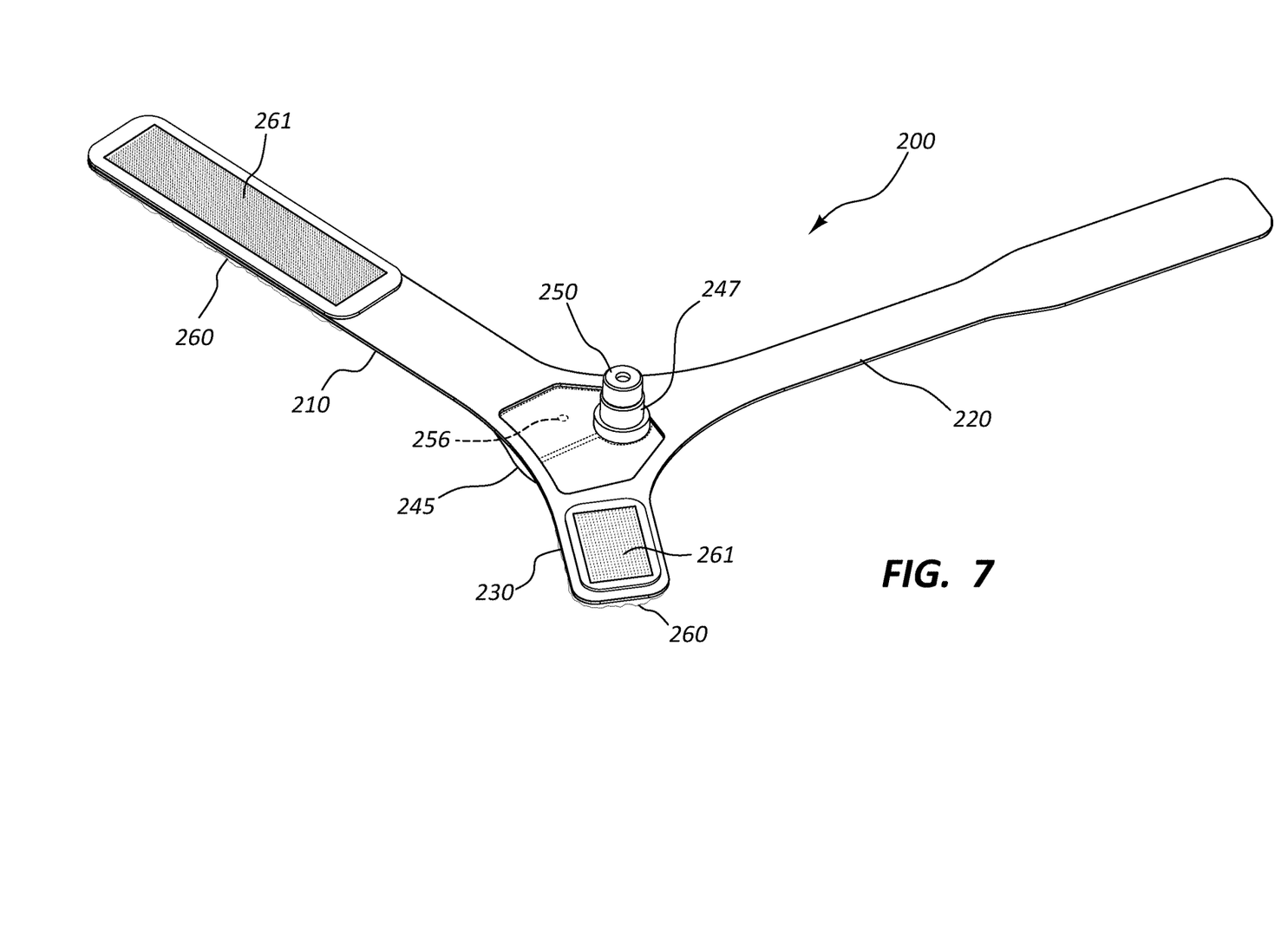
FIG. 7 is a perspective view of a right hand configuration of a hemostasis device analogous to the hemostasis device of FIG. 4A.

The inflation port 247 may comprise a valve member 251 and a cap 250 configured to retain the valve member 251 with the inflation port 247. The inflation port 247 may be configured to be releasably coupled to a medical device, such as a syringe 262, as shown in FIG. 6. When coupled to the syringe, the valve member 251 may be axially displaced such that the inflation port 247 is open and air or fluid may be injected into the inflation chamber 255 of the bladder 245 to inflate the compression member 240 to provide a compressive force at the puncture site. Additionally, air or fluid may be removed from the inflation chamber 255 to deflate the compression member 140 and reduce compression of the puncture site. In certain embodiments the valve member 151 may comprise a pre-slit septum such that an access device coupled to the syringe 262 can penetrate the septum to access the inflation port 247. In other embodiments, the hemostasis device 200 may comprise any suitable configuration of a two-way valve member 251, such as a stopcock, a slit septum, a pinch valve, a slide clamp, etc.

With continued reference to FIGS. 4A-5B, the hand band 210 may comprise a first end 211, a second end 212, and a body portion 213. The hand band 210 may be formed from a flexible material, such as a plastic film, cloth, etc. The hand band 210 may comprise a releasable securement mechanism, such as a hook-and-loop material comprised of a loop material 260 configured to attach to a hook material 261. In some embodiments, the loop material 260 and/or the hook material 261 may be integral to the material of the hand band 210. In other embodiments, the loop material 260 and/or the hook material 261 may be coupled to a top surface and/or bottom surface of the hand band 210 using any suitable technique, such as sonic welding, heat welding, adhesives, etc. The loop material 260 and/or the hook material 261 may cover the top or bottom surfaces of the hand band 210 from the first end 211 to the second end 212. In other embodiments, the loop material 260 and/or the hook material 261 may cover a portion of the hand band 210. For example, as illustrated in FIGS. 4A-5A, the loop material 260 is shown to cover the bottom surface of the hand band 210 from the first end 211 to the second end 212. The hook material 261 is shown to cover a portion of the top surface adjacent the second end 212. Other types of releasable securement mechanisms, such as pressure sensitive adhesives, buckles, magnets, snaps, clasps, etc., are contemplated to be within the scope of this disclosure.

The hand band 210 may be fixedly coupled to the compression member 240 such that the hand band 210 extends outwardly from the first side 241 of the compression member 240 opposite the securement band 230 at angle α relative to the thumb band 220 and angle β relative to the securement band 230. Angle α may range from 15 degrees to 120 degrees, including 30 degrees to 110 degrees, 70 degrees to 120 degrees, 90 degrees to 120 degrees, or ranges including angles of greater than 90 degrees, greater than 100 degrees, and greater than 110 degrees. Angle β may range from 120 degrees to 180 degrees including 140 degrees to 170 degrees, 150 degrees to 160 degrees, or ranges of 180 degrees or less, 170 degrees or less, and 160 degrees or less.

The body 213 of the hand band 210 may form a rectangular shape with a long edge 214 extending away from the compression member 240. The second end 212 may comprise rounded corners such that the second end 212 is atraumatic to the skin of the patient.

In some embodiments, the thumb band 220 comprises a first end 221, a second end 222, and a body portion 223. The thumb band 220 may be configured to prevent displacement of the hemostasis device 200 from a larger diameter portion of the hand, wrist, or foot of a patient to a smaller diameter portion of the hand, wrist, or foot. The thumb band 220 may be formed from a flexible material, such as a plastic film, cloth, etc. The thumb band 220 may comprise a releasable securement mechanism, such as a hook-and-loop material comprised of the loop material 260 and the hook material 261. In some embodiments, the loop material 260 and the hook material 261 may be integral to the material of the thumb band 220. In other embodiments, the loop material 260 and the hook material 261 may be coupled to a top surface and/or bottom surface of the thumb band 220 using any suitable technique, such as sonic welding, heat welding, adhesives, etc. The loop material 260 and the hook material 261 may cover the top or bottom surfaces of the thumb band 220 from the first end 221 to the second end 222. In other embodiments, the loop material 260 and the hook material 261 may cover a portion of the thumb band 220. For example, as illustrated in FIGS. 4A-5A, the loop material 260 is shown to cover the bottom surface of the thumb band 220 from the first end 221 to the second end 222. Other types of releasable securement mechanisms, such as pressure sensitive adhesives, buckles, magnets, snaps, clasps, etc., are contemplated to be within the scope of this disclosure.

The thumb band 220 may be fixedly coupled to the compression member 240 such that the thumb band 220 extends outwardly from the second edge 242 of the compression member 240 between the hand band 210 and the securement band 230 at an angle α relative to the hand band 210 and angle χ relative to the securement band 230. Angle χ may range from 15 degrees to 120 degrees, including 30 degrees to 110 degrees, 70 degrees to 100 degrees or ranges of 90 degrees plus or minus 10 degrees.

The body 223 of the thumb band 220 may form a rectangular shape with a long edge 224 extending away from the compression member 240. The second end 222 may be wider than the first end 221 and comprise rounded corners such that the second end 222 is atraumatic to the skin of the patient.

The securement band 230 may comprise a first end 231, a second end 232, and a body portion 233. The securement band 230 may be formed from a flexible material, such as a plastic film, cloth, etc. The securement band 230 may comprise a releasable securement mechanism, such as a hook-and-loop material comprised of the loop material 260 and the hook material 261. In some embodiments, the loop material 260 and the hook material 261 may be integral to the material of the securement band 230. In other embodiments, the loop material 260 and the hook material 261 may be coupled to a top surface and/or bottom surface of the securement band 230 using any suitable technique, such as sonic welding, heat welding, adhesives, etc. The loop material 260 and the hook material 261 may cover the top or bottom surfaces of the securement band 230 from the first end 231 to the second end 232. In other embodiments, the loop material 260 and the hook material 261 may cover a portion of the securement band 230. For example, as illustrated in FIGS. 4A, 4B, and 5A the loop material 260 is shown to cover the bottom surface of the securement band 230 from the first end 231 to the second end 232. The hook material 261 is shown to cover the top surface from the first end 231 to the second end 232. Other types of releasable securement mechanisms, such as pressure sensitive adhesives, buckles, magnets, snaps, clasps, etc., are contemplated to be within the scope of this disclosure.

The securement band 230 may be fixedly coupled to the compression member 240 such that the securement band 230 extends outwardly from the third edge 243 of the compression member 240 opposite the hand band 210 at an angle χ relative to the thumb band 220 and angle α relative to the hand band 210.

The body 233 of the securement band 230 may form a rectangular shape with a long edge 234 extending away from the compression member 240. The securement band 230 may be shorter in length than the hand band 210. In other embodiments, the securement band 230 may be equivalent to or longer in length than the hand band 210. The second end 232 may comprise rounded corners such that the second end 232 is atraumatic to the skin of the patient.

In certain embodiments, the hemostasis device 200 may not include a thumb band 220. In other embodiments, the hemostasis device 200 may not include a securement band 230. In such an embodiment, the hand band 210 may be formed of an elastomeric material with the first end 211 coupled to the first edge 241 and the second end 212 coupled to the third edge 243. In some embodiments, the hemostasis device 200 may comprise more than three bands. For example, the hemostasis device may comprise 4, 5, or 6 bands.

The hemostasis device 200 may be configured to be a left hand device or a right hand device such that the hemostasis device 200 may provide hemostasis at a distal radial artery puncture site in the left or right hand. FIG. 6 illustrates a hemostasis device 200 configured for use on the left hand of the patient. Viewing the hemostasis device 200 toward the thumb band 220, the hand band 210 extends to the right from the compression member 240 and the inflatable bladder 255 is positioned on the right portion of the top plate 244. When configured for use on the right hand of a patient, such as the embodiment illustrated in FIG. 7, the hand band 220 extends to the left from the compression member 240 when viewing the hemostasis device 200 toward the thumb band 220 and the inflatable bladder 255 is positioned on the left portion of the top plate 244. The hemostasis device 200 configured for the left hand is a mirror image of the hemostasis device configured for the right hand. The elements of the left and right hand hemostasis devices are analogous mirror images, and are thus indicated by common reference numerals in FIGS. 6 and 7.

Figure 8:
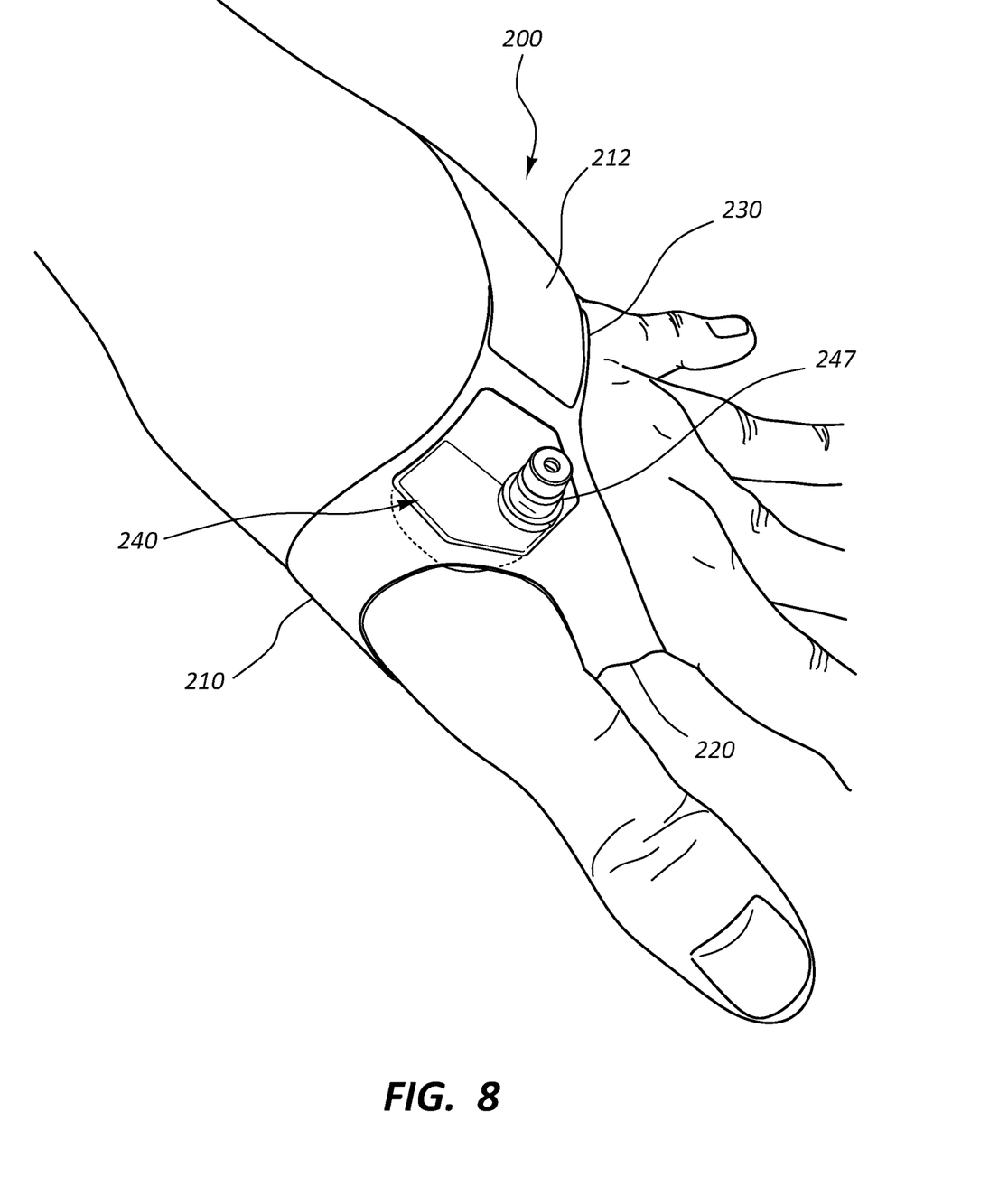
FIG. 8 is a view of the hemostasis device of FIG. 4A positioned on a hand of a patient with a compression member over a puncture site in the distal radial artery.

Referring to FIG. 8, in some embodiments the hemostasis device 200 may be configured to fit around a proximal portion of a hand and around a thumb to provide compression to a vascular access puncture site of a distal portion of a radial artery in the anatomical snuffbox area of a patient's hand. In this use, compression member 240 is positioned over the puncture site of the hand. For example, the compression member may be placed over a puncture site of the distal radial artery in the anatomical snuffbox of the hand. The hand band 210 may be wrapped around the thumb side of the hand, over the palm, and around the lateral side of the hand. The securement band 230 may extend over the back of the hand and the second end 212 of the hand band 210 may be coupled to the second end 232 of the securement band 230. The hemostasis device 200 may comprise an extension member (not shown). The extension member may be comprised of the hook-and-loop material. The extension may be used to couple the hand band 210 to the securement band 230 for patients with large hands. The thumb band 220 may be extended between the thumb and first finger and coupled to the hand band 210 to prevent the hemostasis device 200 from moving proximally to a smaller portion of the hand. In some embodiments, the thumb band 220 may be extended from the compression member 240 between any two fingers of the hand. For example, the thumb band 220 may be extended between the first and second fingers or between the second and third fingers or between the third and fourth fingers.

Figure 9:
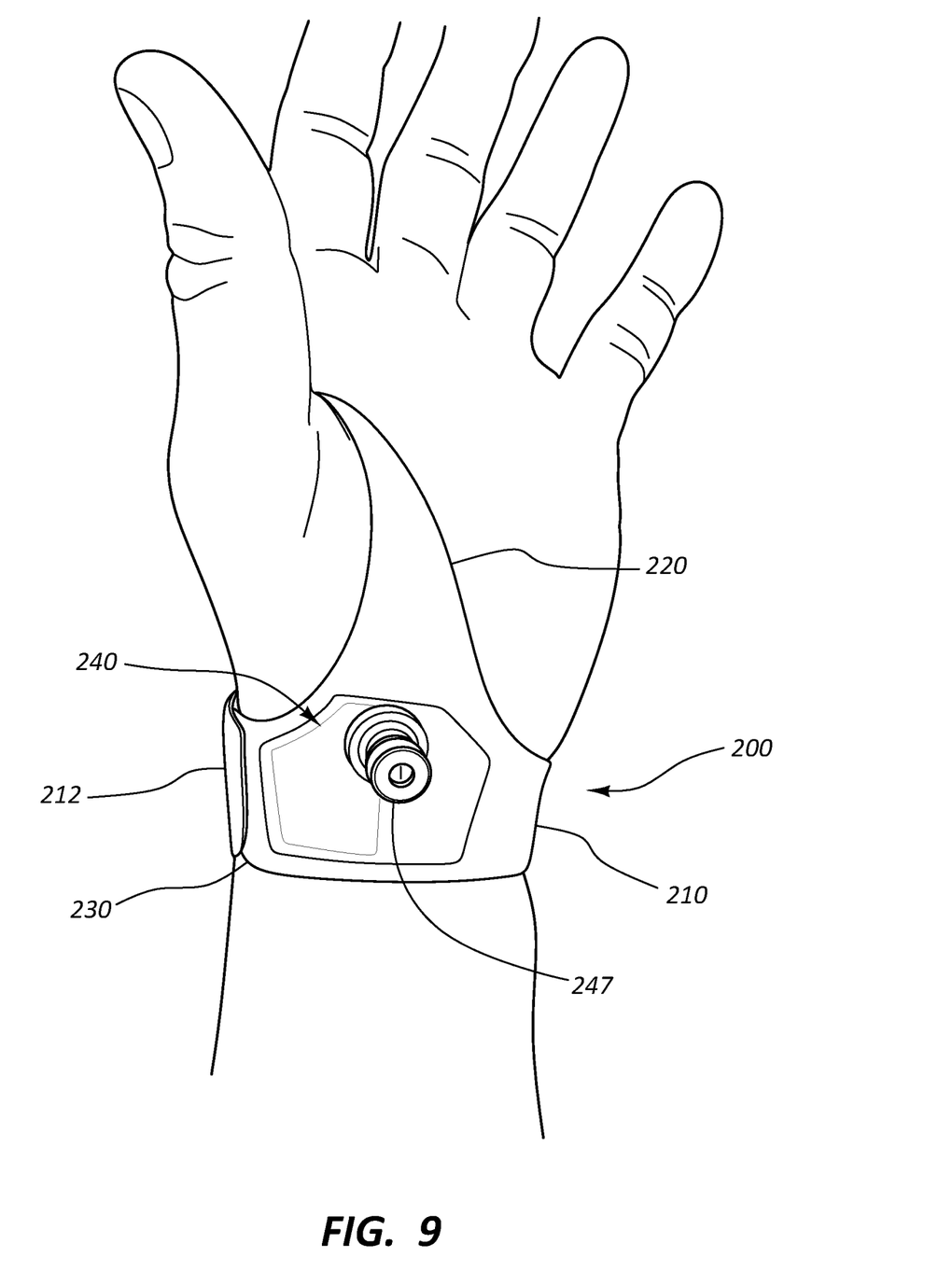
FIG. 9 is a view of the hemostasis device of FIG. 4A positioned on a wrist of the patient with the compression member over a puncture site in the radial artery.

In certain embodiments, as illustrated in FIG. 9, the hemostasis device 200 may be configured to fit around a patient's wrist to provide compression to a vascular access puncture site of the radial artery or other vessels in the wrist area of a patient. In this embodiment, the hand band 210 and securement band 230 extend around the wrist and the second end 212 of the hand band 210 is coupled to the securement band 230. The thumb band 220 extends between the thumb and first finger and couples to the hand band 210 to prevent the hemostasis device 200 from moving proximally on the arm. In some embodiments, the thumb band 220 may not be used to secure the hemostasis device 200 over a puncture site in the wrist area.

Figure 10:
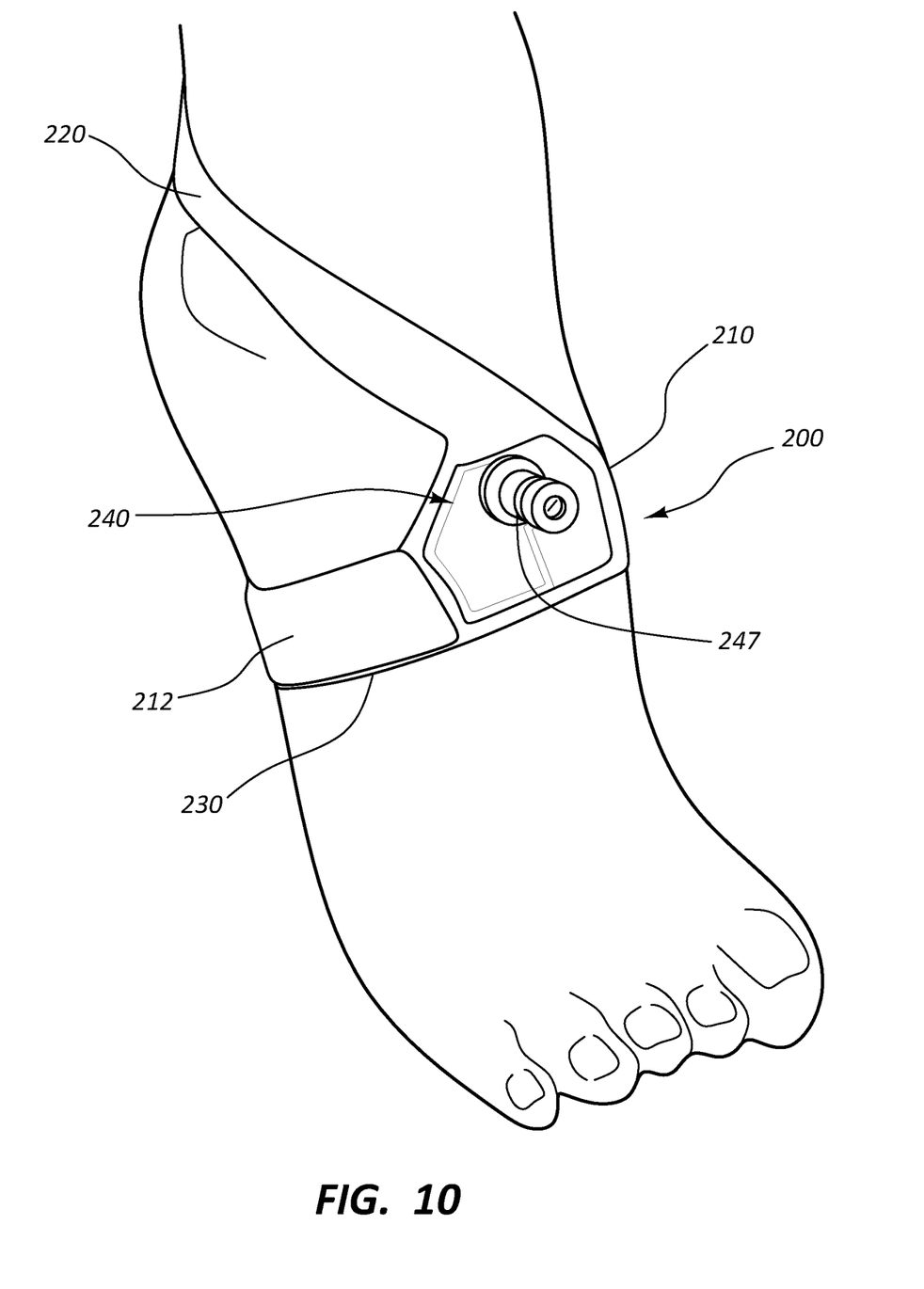
FIG. 10 is a view of the hemostasis device of FIG. 4A positioned on a foot of the patient with the compression member over a puncture site in an artery of the foot of the patient.

In certain embodiments, as illustrated in FIG. 10, the hemostasis device 200 may be used to provide compression to a puncture site on the foot. In this embodiment, the hand band 210 and securement band 230 extend around the foot and the second end 212 of the hand band 210 is coupled to the securement band. The thumb band 220 extends around the heel and couples to the hand band 210 to prevent the hemostasis device 200 from moving distally on the foot.

In some embodiments, a diagnostic or interventional procedure may be performed by the healthcare worker on the patient where access to the distal radial artery in the anatomical snuffbox area of the left hand is achieved utilizing a needle. The distal radial artery of the left hand may be chosen by the healthcare worker to avoid discomfort to the right hand of a right handed patient, to protect the radial artery near the wrist from trauma caused by the procedure, and to facilitate use of the right hand of a right handed healthcare worker while accessing the left distal radial artery. Additionally, the equipment in a surgical suite may be set up on the right side of the patient. Accessing the distal radial artery of the left hand allows the patient to comfortably lay his or her arm across the abdomen. In other embodiments, the healthcare worker may choose to access a patient's vascular system at any suitable site, such as the arteries of the wrist or foot, to perform the interventional diagnostic or therapeutic procedure.

At the conclusion of the interventional diagnostic or therapeutic procedure, compressive pressure may be applied to the puncture site of a vessel of the hand, wrist, or foot to facilitate hemostasis of the puncture site as quickly as possible and without loss of a significant blood volume. The hemostasis device (100 of FIG. 1 or 200 of FIG. 4B) may be utilized to apply the compressive force to the puncture site. In use, the compression member may be positioned over the puncture site with the target centered over the puncture site. The hand band may be wrapped around the hand, wrist, or foot and coupled to the securement band. The thumb band may extend toward a space between the thumb and the first finger and coupled to the hand band. Following application of the hemostasis device, the syringe may be coupled to the port and air or fluid injected into the inflatable bladder such that the inflatable bladder is inflated and applies a compressive force to the puncture site. When hemostasis is achieved, the syringe may be coupled to the inflation port to remove all or a portion of the air or fluid within the bladder such that the bladder is fully or partially deflated.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A hemostasis device, comprising:
   a compression member configured to compress a vascular puncture site;
   a hand band coupled to a first side of the compression member;
   a thumb band coupled to a second side of the compression member; and
   a securement band coupled to a third side of the compression member,
   wherein the hemostasis device is configured to dispose the compression member adjacent a distal radial artery puncture site within the anatomical snuffbox of a hand of a patient,
   wherein the thumb band comprises a body portion,
   wherein a width of a first portion of the body portion nearest the compression member is narrower than a width of a second portion of the body portion remote from the compression member, and
   wherein the first portion is configured to fit between a thumb and a first finger of a patient's hand when the thumb band is wrapped around the thumb.

2. The hemostasis device of claim 1, wherein the compression member comprises a compression mechanism configured to apply a compressive force to the puncture site.

3. The hemostasis device of claim 2, wherein the compression mechanism comprises: a top plate; an inflatable bladder coupled to a bottom surface of the top plate; and an inflation port in fluid communication with the inflatable bladder.

4. The hemostasis device of claim 3, wherein the inflation port comprises a valve member coupled to the top plate.

5. The hemostasis device of claim 2, wherein the compression mechanism comprises a threaded post.

6. The hemostasis device of claim 1, wherein the hand band is configured to releasably couple to the securement band.

7. The hemostasis device of claim 1, wherein the thumb band is configured to releasably couple to the hand band.

8. The hemostasis device of claim 1, wherein an angle of the thumb band relative to the securement band is adjustable from 15 degrees to 120 degrees.

9. A hemostasis device, comprising:
   a compression member configured to compress a vascular access puncture site of a distal portion of the radial artery within the anatomical snuffbox of a hand of a patient;
   a first band coupled to a first side of the compression member;
   a second band coupled to a second side of the compression member; and
   a third band coupled to a third side of the compression member,
   wherein the second band comprises a body portion,
   wherein a width of a first portion of the body portion nearest the compression member is narrower than a width of a second portion of the body portion remote from the compression member, and
   wherein the first portion is configured to fit between a thumb and a first finger of a patient's hand when the second band is wrapped around the thumb.

10. The hemostasis device of claim 9, wherein the first band is configured to extend around a proximal portion of a hand or a wrist of a patient.

11. The hemostasis device of claim 9, wherein the first band is configured to releasably couple to the third band.

12. The hemostasis device of claim 9, wherein the compression member comprises a compression mechanism.

13. The hemostasis device of claim 12, wherein the compression mechanism comprises:
   a top plate;
   an inflatable bladder coupled to a bottom surface of the top plate; and
   an inflation port in fluid communication with the inflatable bladder.

14. The hemostasis device of claim 13, wherein the inflation port comprises a valve member coupled to the top plate.

15. The hemostasis device of claim 12, wherein the compression mechanism comprises a threaded post.

* * * * *